(12) United States Patent
Nilsson (10) Patent No.: US 7,794,478 B2
(45) Date of Patent: Sep. 14, 2010

(54) POLYAXIAL CROSS CONNECTOR AND METHODS OF USE THEREOF

(75) Inventor: Carl Michael Nilsson, Cleveland Heights, OH (US)

(73) Assignee: Innovative Delta Technology, LLC, Cleveland Heights, OH (US)

( * ) Notice: Subject to any disclaimer, the term of this patent is extended or adjusted under 35 U.S.C. 154(b) by 792 days.

(21) Appl. No.: 11/623,180

(22) Filed: Jan. 15, 2007

(65) Prior Publication Data

US 2008/0172093 A1    Jul. 17, 2008

(51) Int. Cl.
*A61B 17/70* (2006.01)
(52) U.S. Cl. .................. 606/251; 606/246; 606/279
(58) Field of Classification Search .............. 606/246, 606/250–253, 278–279, 86 A, 264–277; 623/17.11–17.16; 403/84
See application file for complete search history.

(56) References Cited

U.S. PATENT DOCUMENTS

| | | | |
|---|---|---|---|
| 5,207,678 A | 5/1993 | Harms et al. | |
| 5,312,405 A * | 5/1994 | Korotko et al. | 606/252 |
| 5,360,431 A | 11/1994 | Puno et al. | |
| 5,466,237 A | 11/1995 | Byrd, III et al. | |
| 5,474,555 A | 12/1995 | Puno et al. | |
| 5,496,321 A | 3/1996 | Puno et al. | |
| 5,536,268 A | 7/1996 | Griss | |
| 5,624,442 A | 4/1997 | Mellinger et al. | |
| 5,647,873 A | 7/1997 | Errico et al. | |
| 5,669,911 A | 9/1997 | Errico et al. | |
| 5,690,630 A | 11/1997 | Errico et al. | |
| 5,733,285 A | 3/1998 | Errico et al. | |
| 5,733,286 A | 3/1998 | Errico et al. | |
| 5,782,833 A | 7/1998 | Haider | |
| 5,797,911 A | 8/1998 | Sherman et al. | |
| 5,879,350 A | 3/1999 | Sherman et al. | |
| 5,885,286 A | 3/1999 | Sherman et al. | |
| 5,910,142 A | 6/1999 | Tatar | |
| 5,947,967 A | 9/1999 | Barker | |
| 5,964,760 A | 10/1999 | Richelsoph | |
| 6,053,917 A | 4/2000 | Sherman et al. | |

(Continued)

OTHER PUBLICATIONS

Aesculap, Inc., S4 Spinal System, Sales literature, 2004, Aesculap, printed in U.S.A.

(Continued)

*Primary Examiner*—Eduardo C Robert
*Assistant Examiner*—Steven J Cotroneo
(74) *Attorney, Agent, or Firm*—Hahn Loeser & Parks, LLP; John J. Cunniff (57) ABSTRACT

A connector device for a spinal stabilization apparatus comprises a first elongated member having first and second ends, and is adapted to engage a first spinal stabilizer rod proximal to the first end of the elongated member and is further adapted to engage a spinal cross connector rod proximal to a second end of the first elongated member. The first end of the first elongated member comprises a hook shape and a ferrule and may engage the first spinal stabilizer rod within about 20 degrees of perpendicular to the spinal stabilizer rod in any direction. The ferrule is adapted to be seated within the hook shape and is further adapted to engage the first spinal stabilizer rod. A second elongated member substantially similar to the first may additionally be used in a spinal stabilization apparatus. The connector device may be used in a method of treating a patient.

12 Claims, 5 Drawing Sheets

U.S. PATENT DOCUMENTS

| | | |
|---|---|---|
| 6,113,601 A | 9/2000 | Tatar |
| 6,287,311 B1 | 9/2001 | Sherman et al. |
| 6,402,749 B1 | 6/2002 | Ashman |
| 6,485,494 B1 | 11/2002 | Haider |
| 6,540,748 B2 | 4/2003 | Lombardo |
| 6,565,567 B1 | 5/2003 | Haider |
| 6,626,908 B2 | 9/2003 | Cooper et al. |
| 6,709,434 B1 | 3/2004 | Gournay et al. |
| 6,716,214 B1 | 4/2004 | Jackson |
| 6,733,502 B2 | 5/2004 | Altarac et al. |
| 6,740,086 B2 | 5/2004 | Richelsoph |
| 6,755,830 B2 | 6/2004 | Minfelde et al. |
| 6,869,433 B2 | 3/2005 | Glascott |
| 6,974,460 B2 | 12/2005 | Carbone et al. |
| RE39,089 E | 5/2006 | Ralph et al. |
| 2001/0023350 A1 | 9/2001 | Chio |
| 2002/0010467 A1 | 1/2002 | Cooper et al. |
| 2002/0035366 A1 | 3/2002 | Walder et al. |
| 2002/0151900 A1 | 10/2002 | Glascott |
| 2003/0028192 A1* | 2/2003 | Schar et al. .................. 606/61 |
| 2003/0032957 A1 | 2/2003 | McKinley |
| 2003/0199873 A1 | 10/2003 | Richelsoph |
| 2004/0097933 A1 | 5/2004 | Lourdel et al. |
| 2004/0158247 A1 | 8/2004 | Sitiso et al. |
| 2004/0193160 A1 | 9/2004 | Richelsoph |
| 2004/0215190 A1* | 10/2004 | Nguyen et al. ................ 606/61 |
| 2004/0236330 A1 | 11/2004 | Purcell et al. |
| 2004/0249380 A1 | 12/2004 | Glascott |
| 2004/0267264 A1 | 12/2004 | Konieczynski et al. |
| 2005/0038430 A1 | 2/2005 | McKinley |
| 2005/0049588 A1 | 3/2005 | Jackson |
| 2005/0055026 A1 | 3/2005 | Biedermann |
| 2005/0080415 A1 | 4/2005 | Keyer et al. |
| 2005/0090821 A1* | 4/2005 | Berrevoets et al. ............ 606/61 |
| 2005/0187548 A1 | 8/2005 | Butler et al. |
| 2005/0192571 A1 | 9/2005 | Abdelgany |
| 2005/0192572 A1 | 9/2005 | Abdelgany |
| 2005/0192573 A1 | 9/2005 | Abdelgany |
| 2005/0261687 A1 | 11/2005 | Garamszegi |
| 2006/0036242 A1 | 2/2006 | Nilsson et al. |
| 2006/0036244 A1 | 2/2006 | Spitler et al. |
| 2006/0036252 A1 | 2/2006 | Baynham et al. |
| 2006/0058787 A1 | 3/2006 | David |
| 2006/0058788 A1 | 3/2006 | Hammer et al. |
| 2006/0058880 A1 | 3/2006 | Wysocki et al. |
| 2006/0084996 A1 | 4/2006 | Metz-Stavenhagen |
| 2006/0100622 A1 | 5/2006 | Jackson |
| 2006/0149241 A1 | 7/2006 | Richelsoph et al. |
| 2006/0149372 A1 | 7/2006 | Paxson et al. |
| 2006/0155278 A1 | 7/2006 | Warnick |
| 2006/0247626 A1* | 11/2006 | Taylor et al. .................. 606/61 |
| 2007/0233066 A1* | 10/2007 | Rezach ........................ 606/61 |

OTHER PUBLICATIONS

Surgical Dynamics, Inc., Spiral Radius 90D, Sales literature, 2001, Surgical Dynamics, Inc., printed in U.S.A.

* cited by examiner

POLYAXIAL CROSS CONNECTOR AND METHODS OF USE THEREOF

BACKGROUND OF THE INVENTION

This invention relates to fixation devices for the spinal column. More particularly, this invention relates to a connector for connecting spinal stabilization rods located on opposing sides of the spinal column in a spinal fixation device and associated components. Specifically, this invention relates to a cross connector system that allows for connection of spinal stabilization rods located on opposite sides of the spinal column even when the rods are oriented along axis that do not intersect.

The spine formed of a series of bones called vertebrae. There are 33 vertebrae, which are grouped as cervical, thoracic, lumbar, sacral, and coccygeal vertebrae, according to the regions of the spine they occupy. A typical vertebra consists of two essential parts, an anterior segment or body, and a posterior part, or vertebral or neural arch. These two parts enclose a foramen, the vertebral foramen. Together, the vertebral foramen of the vertebrae form a canal for the protection of the spinal cord. The vertebral arch consists of a pair of pedicles and a pair of laminae.

The body is the largest part of a vertebra, and is more or less cylindrical in shape. Its upper and lower surfaces are flattened. In front, the body is convex from side to side and concave from above downward. Behind, it is flat from above downward and slightly concave from side to side. The pedicles are two short, thick processes, which project backward, one on either side, from the upper part of the body, at the junction of its posterior and lateral surfaces.

Over the years, various techniques and systems have been developed for correcting spinal injuries and/or degenerative spinal processes. Spinal correction frequently requires stabilizing a portion of the spine to facilitate fusing portions of the spine or other correction methodologies. Medical correction of this type is frequently employed for many spinal conditions, such as, for example, degenerative disc disease, scoliosis, spinal stenosis, or the like. Frequently, these corrections also require the use of implants, such as, bone grafts. Stabilizing the spine allows bone growth between vertebral bodies such that a portion of the spine is fused into a solitary unit.

Several techniques and systems have been developed for correcting and stabilizing the spine and facilitating fusion at various levels of the spine. In one type of system, a rod or more commonly, a pair of rods is disposed longitudinally, lateral to each side of the spine and adjacent along the length of the spine in the region of concern. The rod is arranged according to the anatomy and the correction desired. In this system, the rod is aligned along the spine and engages various vertebrae along its length. The rod or rods engage opposite sides of the spine using fixation elements, such as anchors, attached to vertebral bodies by a bone screw that is inserted into the pedicle and penetrates into the body of the vertebra.

Anatomy and correction frequently require aligning the rod and screw at various angles along the length of the portion of correction. In order to provide this alignment, polyaxial screws/anchors have been developed. Many variations of bone screw and rod fixation systems exist on the market today. However, prior systems have been limited in the amount of angulation permitted relative to the place of attachment to the spine. In extreme cases, even with polyaxial screws, the spinal stabilization rods may diverge in their orientation in not just one, but two or even three planes. Such divergence makes connection of the rods difficult. Stated another way, prior cross connector systems typically provided a connector rod that was attached to and extended from the spinal support rods perpendicularly. When the spinal support rods were non-parallel relative to each other, as is often the case, the cross connector system would typically require an additional mid-spine connector piece to join connector rods extending from opposing support rods approximately over the spine. Utilization of such a connector may require the excising of bone to prevent the spinous process of the spine from interfering with placement of the mid-spine connector. Additionally, such connection systems have required multiple components requiring multiple assembly steps during surgery. Also, prior systems have involved the securing of a screw assembly to a cross connector or spinal support rod by direct contact between a set screw and the rod. This contact causes subtle damage to the rod caused by plastic deformation of the rod by the set screw.

Therefore, there is a need for a spinal cross connector assembly that permits a wide range of angulation of spinal support rods relative to the spine and each other while providing an effective and secure lock of the cross connector and rod in the desired position. There is also a need for a mechanism of attachment of opposing spinal stabilizer or support rods to each other that minimizes the possibility of damage by a set screw securing the cross connector to the support rods.

SUMMARY OF THE INVENTION

It is, therefore, an aspect of the present invention to provide a connector device for a spinal stabilization apparatus that provides an increased amount of allowable angulations between spinal stabilizer rods on opposing sides of the spine.

In addition, it is another aspect of the present invention to provide a spinal cross connector assembly that provides a mechanism of attachment of spinal stabilizers or support rods to each other without the spinal stabilizers or support rods sharing a plane of orientation along the axes of the rods.

It is still another aspect of the present invention to provide a cross connector system that utilizes attachment mechanisms that minimize the possibility of damage to the rod by a set screw securing the cross connector to the support rod.

It is still another aspect of the present invention to provide a cross connector that provides a simple method of attachment of opposing support rods located on either side of a spine.

In general, one embodiment of the present invention provides a connector device for a spinal stabilization apparatus that comprises a first elongated member having first and second ends, and is adapted to engage a first spinal stabilizer rod proximal to the first end of the elongated member and is further adapted to engage a spinal cross connector rod proximal to a second end of the first elongated member. The first end of the first elongated member comprises a hook shape and a ferrule and may engage the first spinal stabilizer rod within about 20 degrees of perpendicular to the spinal stabilizer rod in any direction. The edges of the hook shape may also be chamfered to permit angulation of the spinal support rod. The second end of the first elongated member may be adapted to engage the spinal cross connector rod through a slot in the second end, and the slot in the second end of the first elongated member may be further adapted to receive a set screw to secure the cross connector rod in the second end.

The ferrule is adapted to be seated within the hook shape and is further adapted to engage the first spinal stabilizer rod. The hook shape of the first end of the first elongated member may comprise two opposed tabs separated by a first gap which forms an entrance into a channel of the hook shape. The ferrule may have an outside diameter that is greater than the width of the first gap. The first end of the first elongated member may additionally comprise a retainer, such as a spring, for maintaining the ferrule in contact with one or more side walls of the hook shape proximal to the first gap. The elongated member may additionally comprise an aperture, through which a set screw may be inserted to engage the ferrule and secure it in place.

A spinal stabilization apparatus may comprise a connector device as described above and may additionally comprise a second elongated member substantially similar to or even identical to the first elongated member.

The connector device may be used in a method of treating a patient. The method may comprise attaching at least a first longitudinal spinal stabilizer to the spine of a patient, and attaching a first elongated member to the spinal stabilizer. The first elongated member has first and second ends, and the first spinal stabilizer is engaged to the first end of the first elongated member. The first end of the elongated member is adapted to engage the first longitudinal spinal stabilizer within about 20 degrees of perpendicular to the first longitudinal spinal stabilizer in any direction. The first end of the first elongated member comprises a hook shape and a ferrule. The ferrule is adapted to engage the first spinal stabilizer rod and to be seated within the hook shape.

The hook shape of the first end of the first elongated member comprises two opposed tabs separated by a first gap which forms an entrance into a channel of the hook shape. The ferrule may have an outside diameter that is greater than the first gap. A spring or other retainer may be present in the first end of the first elongated member for maintaining the ferrule in contact with one or more side walls of the hook shape proximal to the first gap.

The method of treating a patient may additionally comprise attaching a second longitudinal spinal stabilizer to the spine of a patient and attaching a second elongated member to the second spinal stabilizer. The second elongated member is similar to the first elongated member and may have first and second ends. The second spinal stabilizer may be engaged to the first end of the second elongated member, and the first end of the second elongated member may be adapted to engage the second longitudinal spinal stabilizer within about 20 degrees of perpendicular to the second longitudinal spinal stabilizer in any direction. The first end of the second elongated member may also comprise a hook shape and a ferrule adapted to engage the second spinal stabilizer, with the ferrule being adapted to be seated within the hook shape. The hook shape of the first end of the second elongated member may comprise two opposed tabs separated by a second gap which forms an entrance into a channel of the hook shape. The ferrule may have an outside diameter that is greater than the second gap. The first end of the second elongated member may additionally comprise a spring for maintaining the ferrule in contact with one or more side walls of the hook shape proximal to the second gap.

DETAILED DESCRIPTION OF THE INVENTION

The present invention is directed toward a spinal stabilization apparatus for connecting and immobilizing spinal support rods located laterally on opposite sides of a section of a spine. The apparatus includes first and second hook members. The first hook member is adapted to engage a first longitudinal spinal support stabilizer located laterally to a first side of a section of a spinal column, and the second hook member is adapted to engage a second longitudinal spinal support stabilizer located laterally to a second side of a section of a spinal column. Each of the first and second hook members are also adapted to engage opposite ends of a cross connector rod. First and second hook members may be further adapted to permit angulation of an attached spinal support rod relative to the hook end member. Stated another way, first and second hook end members may be adapted to attach to a spinal support rod at an angle of between about 70 and 90 degrees in any direction, i.e., through an arc of about 40 degrees in any direction centered on a perpendicular attachment to the spinal support rod.

In another embodiment, the first and second hook and members may be adapted to attach to a spinal support rod at an angle between about 75 and 90 degrees, that is, through an arc of about 30 degrees in any direction centered on a perpendicular attachment. In still another embodiment, the first and second hook and members may be adapted to attach to a spinal support rod at an angle between about 80 and 90 degrees, that is, through an arc of about 20 degrees in any direction centered on a perpendicular attachment.

The following examples should not be viewed as limiting the scope of the invention. The claims will serve to define the inventions. Additionally, it should be noted that elements of one example may be combined with elements of another example, except where the function of the components prohibits such combination. The following examples are non-limiting therefore in their arrangements and combinations of elements.

Figure 1A:
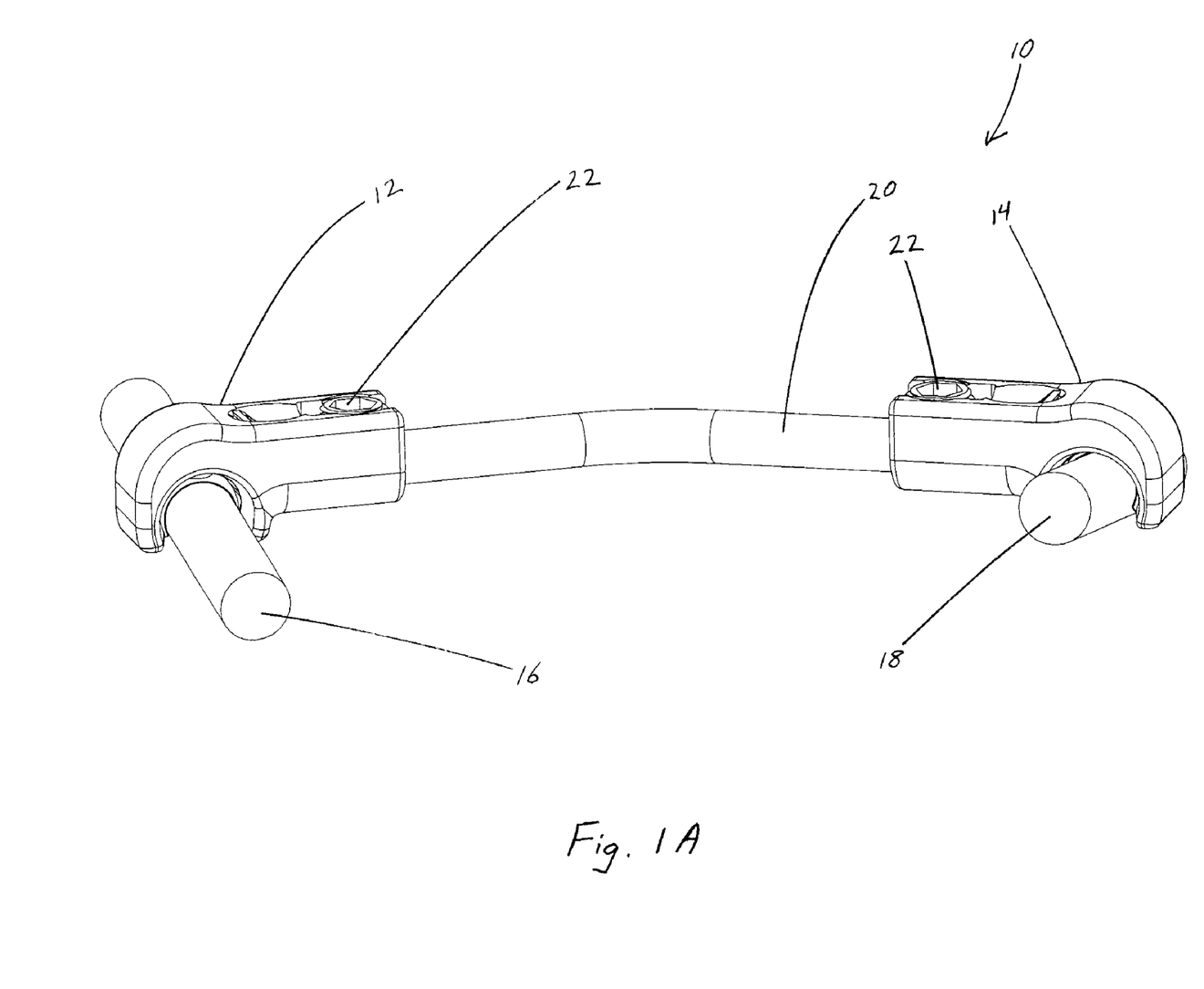
FIG. 1A is a perspective view of the polyaxial cross connector of the present invention.
Figure 1B:
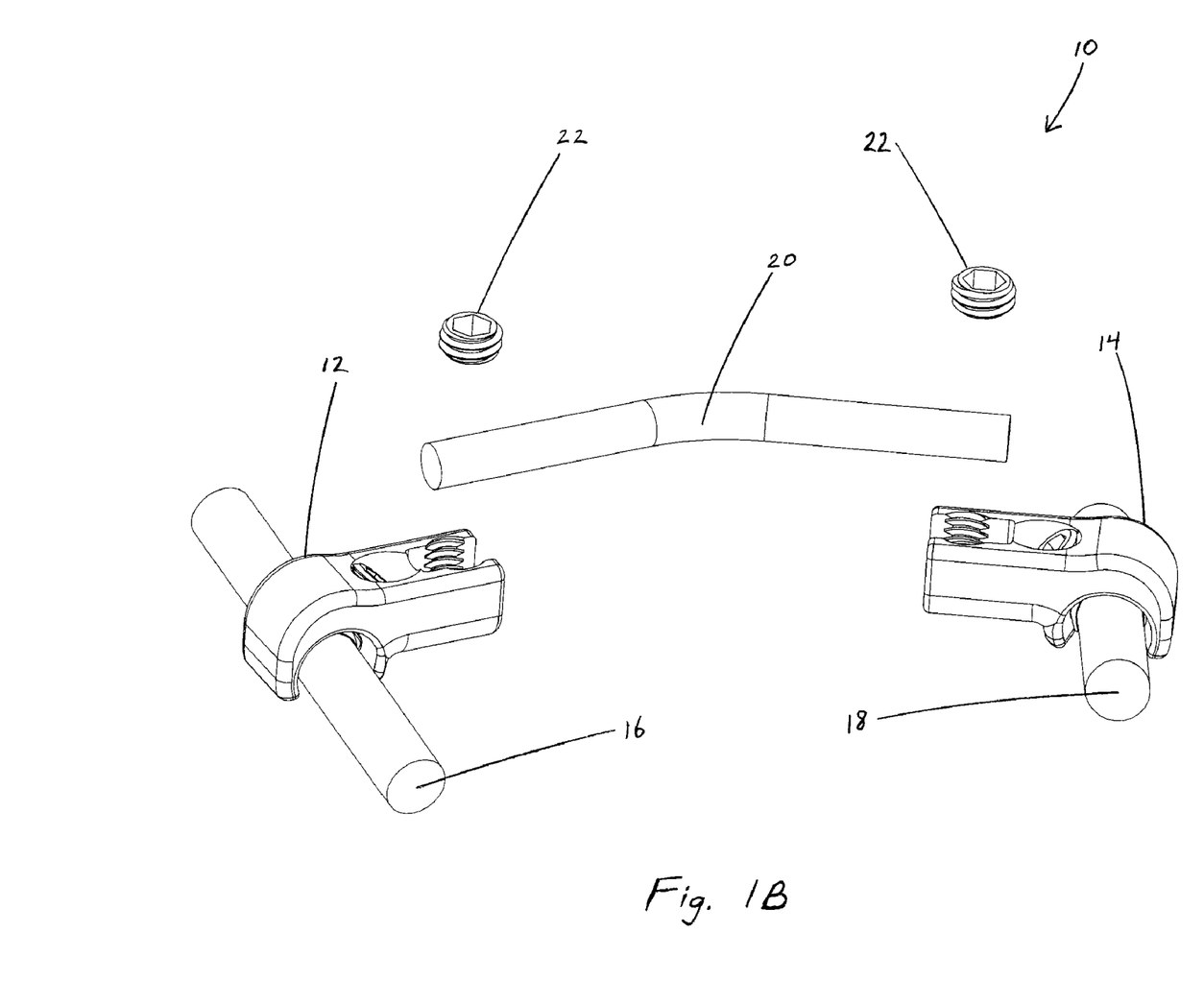
FIG. 1B is a partially exploded view of the embodiment shown in FIG. 1A from an alternate elevation.

As shown in FIGS. 1A and 1B, a spinal stabilization apparatus 10 includes first 12 and second 14 hook members. First hook member 12 is adapted to engage a first longitudinal spinal support stabilizer rod 16 located laterally to a first side of a section of a spinal column, and the second hook member 14 is adapted to engage a second longitudinal spinal support stabilizer rod 18 located laterally to a second side of a section of a spinal column. Each of the first and second hook members 12, 14 are also adapted to engage opposite ends of a cross connector rod 20, which is secured in first and second hook members 12, 14 by set screws 22.

Figure 2A:
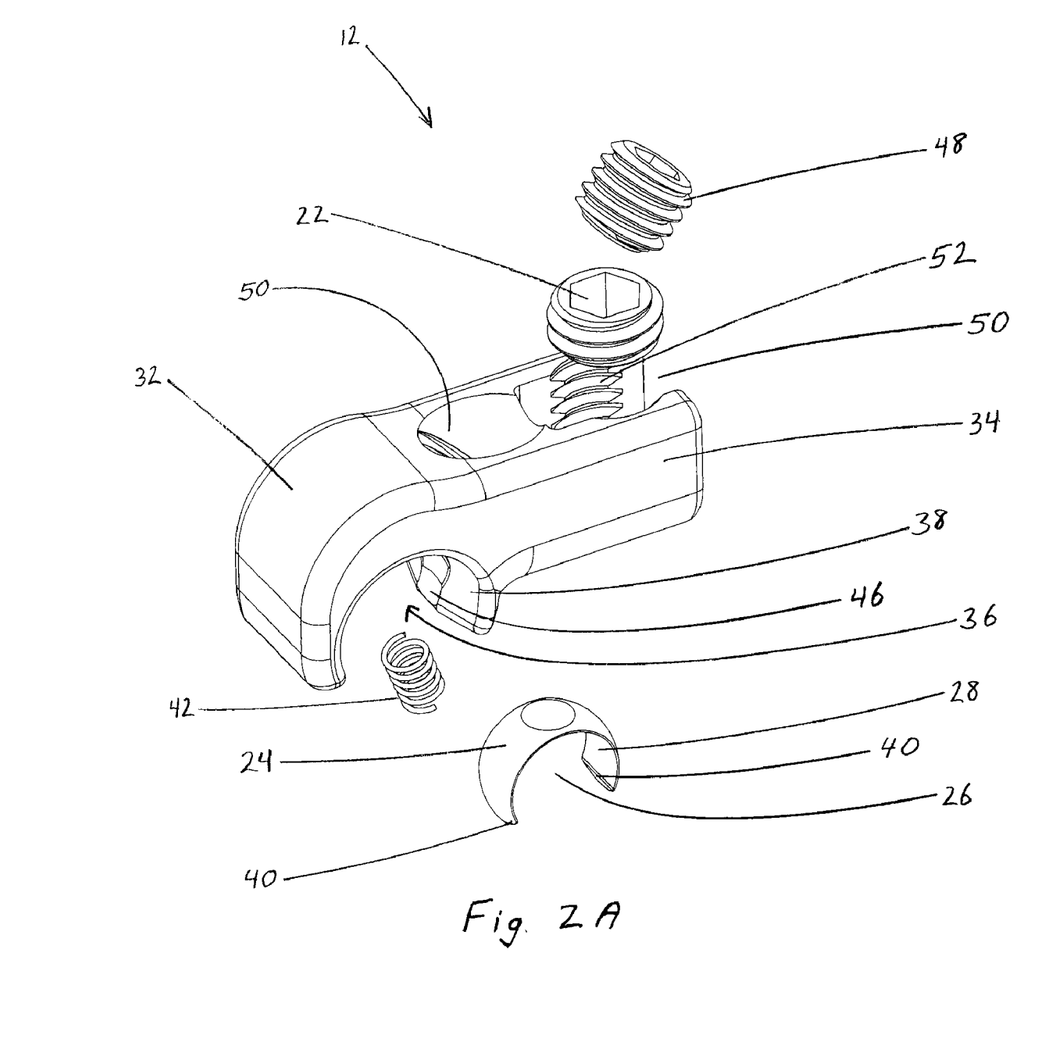
FIG. 2A is an exploded, perspective view of a hook end member of the embodiment of FIG. 1, as assembled.
Figure 2B:
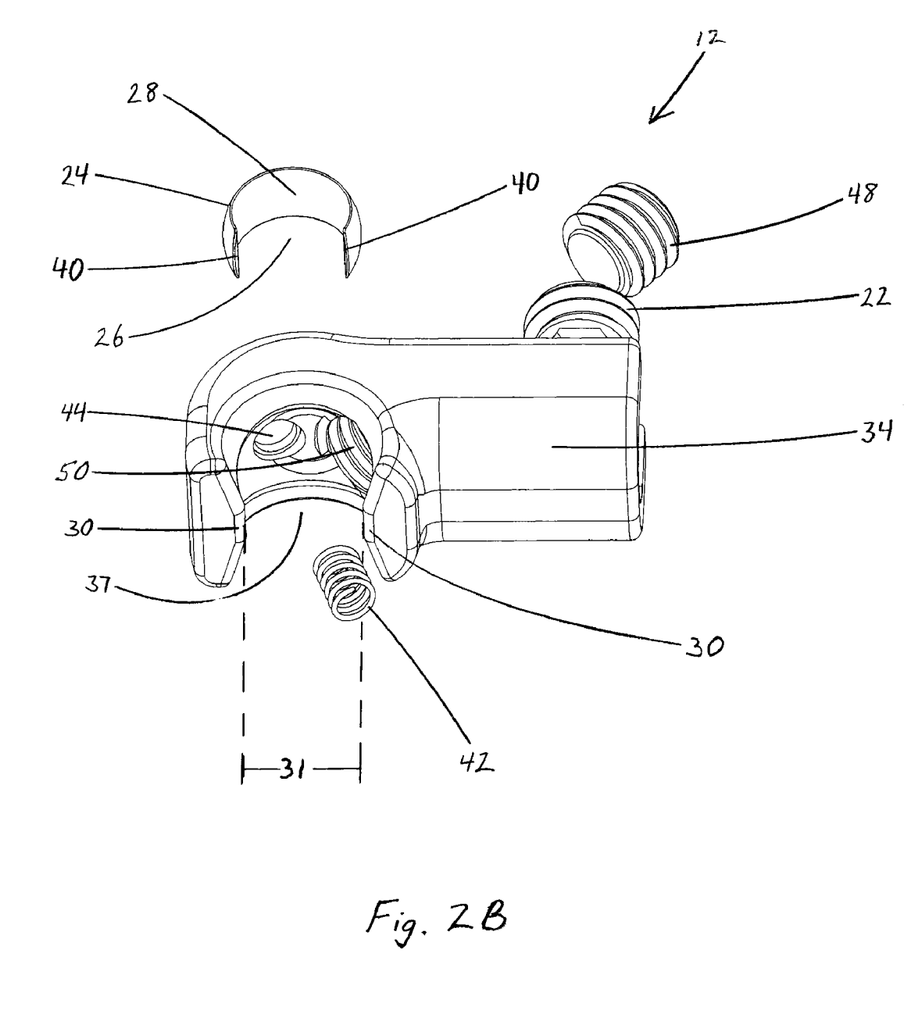
FIG. 2B is an exploded view of the embodiment shown in FIG. 2A from an alternate elevation.
Figure 2C:
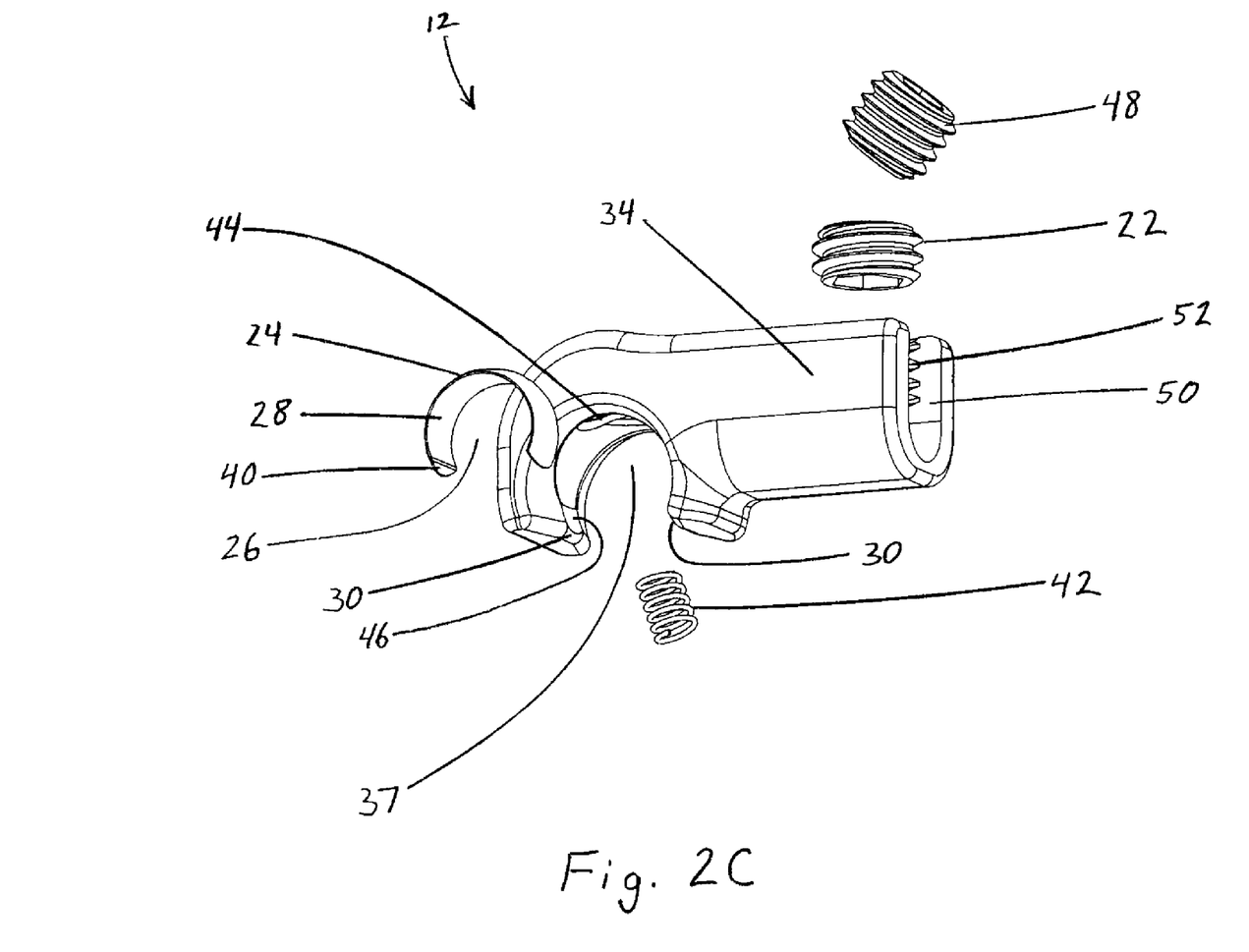
FIG. 2C is an exploded view of the embodiment shown in FIGS. 2A and 2B from an alternate elevation.

FIGS. 2A, 2B and 2C illustrate an arrangement of the first hook member 12. It should be understood, however, that similar or identical structures and components may also present in second hook member 14. Hook member 12 is an elongated structure with a hook end 32 and cross connector end 34 on opposite ends of hook member 12. Hook end 32 may be generally described as hook shaped, comprising a hook end channel 36 passing through the hook shape and entering into a generally spherical cavity 37.

Hook member 12 (and also hook member 14) also includes a ferrule 24, which is C-shaped or generally spherical in shape with a generally cylindrical channel 26 located therethrough, creating an arcuate seat 28 in the walls of channel 26 for receiving a stabilizer such as a rod 16. As a result of the presence of channel 26 in ferrule 24, the open end of ferrule 24 includes two opposed tabs 40 located to each side of channel 26. Tabs 40 are configured in such a way that tabs 40 have a minor amount of flexibility, allowing them to flex outwardly as rod 16 is inserted into and passes into channel 26 and is ultimately secured in seat 28. Channel 26 has a cross-sectional configuration that corresponds to the cross-sectional configuration of rod 16 (or rod 18) such that arcuate seat 28 maintains contact with at least half of the portion of rod 16 that lies within channel 26. In one embodiment, arcuate seat 28 maintains contact with more than half of the circumference of rod 16 that lies within channel 26. In another example, arcuate seat 28 maintains contact with about two thirds or more of the circumference of rod 16 that lies within channel 26. In this manner, any load to be transferred between rod 16 and hook end 32 is distributed as evenly as possible across the length and width of seat 28.

Ferrule 24 is adapted to be seated within cavity 37 in hook end 32 such that rods 16, 18 may be engaged in ferrule 24 and pass through channel 36. Channel 36 is generally cylindrical, with a gap 31 between hook tabs 30 forming an entrance into channel 36 and forming the hook shape of hook end 32. Gap 31 is configured to allow rods 16, 18 to pass into channel 36. In some embodiments, gap 31 is essentially the same distance as the diameter of rods 16, 18. In other embodiments, gap 31 is up to 0.1 mm larger than the diameter of rods 16, 18. Ferrule 24 may be further configured to allow it to be inserted into cavity 37 through channel 36 but with an outside diameter that prevents it from passing through gap 31.

In one example, ferrule 24 has an outside diameter of about 6.5 mm, cavity 37 has a diameter of approximately 6.5 mm, gap 31 is about 5.5 mm wide and the diameter of rods 16, 18 is about 5.5 mm. This provides for the insertion of ferrule 24 into cavity 37 and for the insertion of rods 16, 18 into seat 28 of ferrule 24 through gap 31 but prevents ferrule 24 from passing through gap 31.

Channel 36 may be further adapted to permit rotation of ferrule 24 within channel 36 and thereby allow angulation of spinal support rod 16, 18 within channel 36. One possible adaptation is the presence of chamfered edges 38 surrounding channel 36, allowing ferrule 24 and rod 16, 18 to pivot within channel 36. In one embodiment, rod 16, 18 is capable of pivoting through an arc of approximately 40 degrees in any direction. Stated another way, hook members 12, 14 are adapted to attach to a spinal support rod at an angle of between about 70 and 90 degrees in any direction, i.e., through an arc of about 40 degrees in any direction centered on a perpendicular attachment to the spinal support rods. In another embodiment, hook members 12, 14 are adapted to attach to a spinal rod at an angle of between 75 and 90 degrees in any direction, that is, though an arc of about 30 degrees in any direction centered on a perpendicular attachment. In another embodiment, hook members 12, 14 are adapted to attach to a spinal rod at an angle of between about 80 and 90 degrees in any direction, that is, through an arc of about 20 degrees in any direction centered on a perpendicular attachment. In still another embodiment, hook members 12, 14 are adapted to attach to a spinal rod at an angle of between 85 and 90 degrees in any direction, that is, through an arc of about 10 degrees in any direction centered on a perpendicular attachment.

Hook end 32 also includes a retainer such as spring 42 for maintaining ferrule 24 in channel 36 by keeping ferrule 24 in contact with side wall 46 of cavity 37. As mentioned above, ferrule 24 may be configured such that it can not pass through gap 31. Spring 42 may be seated in a seat 44 within cavity 37. It is also envisioned that other resilient components may be used in place of spring 42. For example, a retainer may take the form of a resilient, flexible tab projecting from the inner wall of cavity 37 (not shown). Alternatively, a Belleville washer (not shown) may also be used as a retainer. Hook members 12 and 14 also each contain an aperture 50, which passes through hook member 12 and accesses cavity 37, allowing set screw 48 to contact ferrule 24, as described more fully below.

Cross connector end 34 of hook members 12, 14 comprises a cavity 50 adapted to receive cross connector rod 20. As in the embodiment shown, cavity 50 may be enclosed on three sides to allow cross connector rod 20 to be inserted into cavity 50 and engage hook member 12 at cross connector end 34. Cavity 50 may also include threads 52 to engage a set screw 54. When cross connector rod 20 is inserted into cavity 50, set screw 54 contacts cross connector rod 20 and secures it in place in cross connector end 34.

As mentioned above, ferrule 24, cavity 37 and channel 36 are adapted to permit rod 16 to pivot within channel 36. In one embodiment, rod 16 is capable of rotating through an arc of approximately 40 degrees in any direction. Likewise, the identical structures in second hook member 14 permit rod 18 to be angulated through an arc of approximately 40 degrees in any direction, with the arc centered on a perpendicular attachment. Stated another way, rods 16, 18 may be angulated through hook members 12, 14 not only side-to-side, or up-and-down relative to the central axis of hook members 12, 14, but both side-to-side and up-and-down simultaneously. In this way, support rods 16 and 18 may be angled a total of up to 40 degrees from parallel in any direction while still directly connecting the first and second hook members 12, 14 with a substantially straight cross connector rod 20. In those situations where rods 16 and 18 are angled more than 40 degrees from parallel to each other, a connection may still be directly made between first and second hook members 12, 14 with a single cross connector rod 20. In such a case, cross connector rod 20 may be bent with an instrument for bending spinal rods, such as an instrument known in the art as a French Bender (not shown), to accommodate the greater angulation. Therefore, even in cases where there is greater than 40 degrees of angulation in any direction, relative to a parallel condition between the rods, the present invention provides an apparatus and method for spinal stabilization utilizing only a single cross connector rod without the need for an intervening connector piece located between the hook members, thereby directly connect hook members 12 and 14 without an intervening connector. The absence of an additional connector other than those directly connected to the spinal support rods, i.e. hook members 12 and 14, permits spinal stabilization with a decreased or even eliminated need for excision of bone, such as the spinous process, to permit installation of the stabilization system.

In use, the cross connector system of the present invention would be utilized after spinal stabilization rods 16, 18 have been secured to the spine using bone screws, such as pedicle screws. Hook members 12 and 14 would typically be partially assembled prior to surgery, with ferrule 24 positioned within channel 36 and held in place by spring 42 or other similar structures. Hook member 12 would be attached to rod 16 by sliding hook member over rod 16 and positioning a portion of rod 16 within channel 26. As stated above, ferrule 24 is oriented in cavity 37 such that channel 26 cooperates with channel 36 of hook member 12 to permit alignment of rod 16 or rod 18 through both ferrule channel 26 and hook end channel 36. When rod 16 is passed through gap 31 and inserted into ferrule 24 in cavity 37, the resilience of spring 42 allows ferrule 24 to be temporarily and reversibly positioned upward into cavity 37, away from side wall 46. This allows tabs 40 to flex outward as rod 16, 18 passes into channel 26 becoming secured against arcuate seat 28. Once rod 16, 18 is secured in seat 28 and pressure against spring 42 is released, spring 42 again applies pressure to ferrule 24, forcing it into contact with side wall 46 and holding it in place there.

Once corresponding first and second hook members 12, 14 are attached to support rods 16, 18, cross connector rod 20 is then inserted into each cavity 50 of cross connector end 34 of hook members 12, 14. As mentioned above, the angulation of hook members 12, 14 relative to a perpendicular position on support rods 16, 18, allows the use of a single cross connector rod 20 between hook members 12 and 14 without resorting to an additional connector located between support rods 16, 18. This allows a surgeon to utilize fewer components in a spinal stabilization system than previously needed. A surgeon may simply select a cross connector rod of appropriate length to connect first and second hook members and bend it the appropriate amount if necessary. Once cross connector 20 is engaged in cavity 50, a set screw 22 may be used to secure cross connector rod 20 in cavity 50.

After cross connector 20 is secured in cavities 50 of hook members 12, 14, any final adjustments to the angulation of rods 16 and 18 may be performed and ferrule 24 may be permanently secured into position with a set screw 48 that is inserted into a set screw aperture 50. In contrast with spring 42, set screw 48 keeps ferrule 24 in constant contact with side wall 46 and does not allow ferrule 24 to move upward into channel 36 away from side wall 46 even temporarily, thereby securing rod 16, 18. The engagement of set screw 48 against ferrule 24 results in ferrule 24 being locked in place with arcuate seat 28 at least partially surrounding rods 16, 18. Set screw 48 does not however, directly engage rods 16, 18. Instead, pressure from set screw 48 is distributed to ferrule 24 and locking pressure is exerted against a relatively large surface area of rods 16, 18 by arcuate seat 28. In this way, set screw 48 does not etch or otherwise deform or damage rods 16, 18 and the possibility of damage to rods 16, 18 during use is minimized or eliminated.

Although it is envisioned that ferrule 24 would ordinarily be permanently secured in place after cross connector 20 is secured in cavities 50, such a sequence of assembly is not necessarily required. For example, in those situations where hook members 12 and 14 are attached to rods 16 and 18 in a substantially perpendicular position, set screw 48 could be utilized as described above to secure ferrule 24 in place before cross connector 20 is secured in place. The present spinal stabilization system may also be adjusted in place after set screws 48 and 22 have been secured in place by loosening one or more set screws, making the necessary adjustments and re-securing the set screws in place.

The present invention provides a self-adjusting spinal stabilization system. Ferrule 24 may rotate within cavity 37 to allow a particular angulation of hook members 12, 14 as dictated by the patient's anatomy until set screws 48 are fully engaged with ferrule 24. This eliminates the need for separate adjustment of a connector in the mid-spine region as with prior systems, which only allow a hook member to attach to a spinal support rod only perpendicularly.

Based upon the foregoing disclosure, it should now be apparent that the polyaxial cross connector assembly of the present invention will carry out the objects set forth hereinabove. It is, therefore, to be understood that any variations evident fall within the scope of the claimed invention and thus, the selection of specific component elements can be determined without departing from the spirit of the invention herein disclosed and described.

I claim:

1. A connector device for a spinal stabilization apparatus, the device comprising:

at least a first elongated member having first and second ends, adapted to engage at least a first spinal stabilizer rod proximal to the first end of the first elongated member and further adapted to engage a spinal cross connector rod proximal to a second end of the first elongated member, wherein the first end of the elongated member is adapted to engage the first spinal stabilizer rod up to about 20 degrees from perpendicular to the first spinal stabilizer rod in any direction, and wherein the first end of the first elongated member comprises a hook shape and a ferrule that is generally spherical in shape with a generally cylindrical channel located therethrough, and wherein the ferrule is adapted to be seated within the hook shape and is further adapted to engage the first spinal stabilizer rod, wherein the hook shape of the first end of the first elongated member comprises two opposed tabs separated by a first gap which forms an entrance into a cavity of the hook shape and wherein the ferrule has an outside diameter that is greater than the width of the first gap at the entrance wherein the first end of the first elongated member additionally comprises a retainer adapted to maintain the ferrule in contact with one or more side walls of the hook shape proximal to the first gap, and wherein the retainer comprises a spring in contact with the ferrule.

2. The connector device of claim 1, wherein the first end of the first elongated member comprises chamfered edges of the hook shape.

3. The connector device of claim 1, additionally comprising a set screw that is adapted to engage the ferrule through an aperture in the first elongated member.

4. The connector device of claim 1, wherein the first elongated member is adapted to engage the spinal cross connector rod through a slot in the second end of first elongated member, and wherein the slot in the second end of the first elongated member is adapted to receive a set screw.

5. A spinal stabilization apparatus comprising a plurality of connector devices according to claim 1.

6. A spinal stabilization apparatus comprising a plurality of connector devices according to claim 2.

7. A spinal stabilization apparatus comprising a plurality of connector devices according to claim 3.

8. A spinal stabilization apparatus comprising a plurality of connector devices according to claim 4.

9. A method of treating a patient, the method comprising:

attaching at least a first longitudinal spinal stabilizer to the spine of a patient; and attaching a first elongated member to the spinal stabilizer;

wherein the first elongated member has first and second ends, and wherein the first spinal stabilizer is engaged to the first end of the first elongated member and further wherein the first end of the elongated member is adapted to engage the first longitudinal spinal stabilizer up to about 20 degrees from perpendicular to the first longitudinal spinal stabilizer in any direction, and wherein the first end of the first elongated member comprises a hook shape and a first ferrule that is generally spherical in shape with a generally cylindrical channel located therethrough, adapted to engage the first spinal stabilizer rod, and wherein the ferrule is adapted to be seated within the hook shape, and wherein the hook shape of the first end of the first elongated member comprises two opposed tabs separated by a first gap which forms an entrance into a channel of the hook shape and wherein the first ferrule has an outside diameter that is greater than the first gap at the entrance, and wherein the first end of the first elongated member additionally comprises a spring in contact with the ferrule for maintaining the first ferrule in contact with one or more side walls of the hook shape proximal to the first gap.

10. The method of claim 9, additionally comprising:

attaching a second longitudinal spinal stabilizer to the spine of a patient; and attaching a second elongated member to the second spinal stabilizer;

wherein the second elongated member has first and second ends, and wherein the second spinal stabilizer is engaged to the first end of the second elongated member, and further wherein the first end of the second elongated member is adapted to engage the second longitudinal spinal stabilizer up to about 20 degrees from perpendicular to the second longitudinal spinal stabilizer in any direction, and additionally wherein the first end of the second elongated member comprises a hook shape and a second ferrule that is generally spherical in shape with a generally cylindrical channel located therethrough adapted to engage the second spinal stabilizer, and wherein the second ferrule is adapted to be seated within the hook shape of the second elongated member.

11. The method of claim 10, wherein the hook shape of the first end of the second elongated member comprises two opposed tabs separated by a second gap which forms an entrance into a channel of the hook shape and wherein the second ferrule has an outside diameter that is greater than the second gap.

12. The method of claim 11, wherein the first end of the second elongated member additionally comprises a spring in contact with the second ferrule for maintaining the second ferrule in contact with one or more side walls of the hook shape proximal to the second gap.

\* \* \* \* \*